(12) United States Patent
Yu et al.

(10) Patent No.: US 7,303,880 B2
(45) Date of Patent: Dec. 4, 2007

(54) MICRODISSECTION-BASED METHODS FOR DETERMINING GENOMIC FEATURES OF SINGLE CHROMOSOMES

(75) Inventors: Jingwei Yu, Madison, WI (US); Zhongxia Qi, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 174 days.

(21) Appl. No.: 11/084,279

(22) Filed: Mar. 18, 2005

(65) Prior Publication Data

US 2006/0211001 A1 Sep. 21, 2006

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3

(58) Field of Classification Search .................. 435/6; 536/23.1, 24.3
See application file for complete search history.

(56) References Cited

U.S. PATENT DOCUMENTS 6,664,057 B2 * 12/2003 Albertson et al. ............. 435/6
2005/0112611 A1 * 5/2005 Helgadottir ................... 435/6

OTHER PUBLICATIONS

Pastinen et al.,Minisequencing : A specific tool for DNA analysis and diagnostics on oligonucleotide arrays. Genome Research 7 : 606-614 (1997).*
Wang et al. Large -scale identification, mapping , and genotyping of Single-Nucleotide polymoprphisms in the human genome. Science 280: 1077-1082 (1998).*
Meltzer et al. Rapid generation of region specific probes by chromosome microdissection and their application.Nature Genetics 1(1) : 24-28 (Apr. 1992).*
Cotter et al. Gene mapping by microdissection and enzymatic amplification : Heterogeneity in Leukemia associated breakpoints on chromosome 11. Gene, Chromosomes & Cancer 3 : 8-15 (1991).*

* cited by examiner

*Primary Examiner*—Ethan Whisenant
(74) *Attorney, Agent, or Firm*—Quarles & Brady LLP

(57) ABSTRACT

The present provides a microdissection-based method for identifying a genomic feature present within a visible chromosome region. The method includes steps of: (a) microdissecting a single copy of a chromosome to obtain a visible chromosome region; (b) amplifying the visible chromosome region to obtain amplified single chromosome DNA; and (c) subjecting the amplified single chromosome DNA to microarray analysis whereby such analysis identifies at least one genomic feature present within the visible chromosome region. The method is applicable to determining genomic features including, but not limited to, genomic DNA size, gene content, DNA breakpoint, or DNA polymorphism (e.g., single nucleotide polymorphisms).

20 Claims, 4 Drawing Sheets

SEQUENCE LISTING

<160> NUMBER OF SEQ ID NOS: 75

<210> SEQ ID NO 1
<211> LENGTH: 20
<212> TYPE: DNA
<213> ORGANISM: Homo sapiens

<400> SEQUENCE: 1
gccagggcat gttttatagg                                               20

<210> SEQ ID NO 2
<211> LENGTH: 20
<212> TYPE: DNA
<213> ORGANISM: Homo sapiens

<400> SEQUENCE: 2
ccactgtttt ggcactgaga                                               20

<210> SEQ ID NO 3
<211> LENGTH: 20
<212> TYPE: DNA
<213> ORGANISM: Homo sapiens

<400> SEQUENCE: 3
tccattccac tcaacacacg                                               20

<210> SEQ ID NO 4
<211> LENGTH: 20
<212> TYPE: DNA
<213> ORGANISM: Homo sapiens

<400> SEQUENCE: 4
caatgacacc caaaaattcg                                               20

<210> SEQ ID NO 5
<211> LENGTH: 26
<212> TYPE: DNA
<213> ORGANISM: Homo sapiens

<400> SEQUENCE: 5
ttgaaagata tccactctct tcttca                                        26

<210> SEQ ID NO 6
<211> LENGTH: 26
<212> TYPE: DNA
<213> ORGANISM: Homo sapiens

<400> SEQUENCE: 6
ggagagtatg ctttacatat caggaa                                        26

<210> SEQ ID NO 7
<211> LENGTH: 20
<212> TYPE: DNA
<213> ORGANISM: Homo sapiens

<400> SEQUENCE: 7
tgatggttgc tgacacttgg                                               20

<210> SEQ ID NO 8
<211> LENGTH: 20
<212> TYPE: DNA
<213> ORGANISM: Homo sapiens

```
<400> SEQUENCE: 8
tgcagtttgc ctatcgtcac                                              20

<210> SEQ ID NO 9
<211> LENGTH: 20
<212> TYPE: DNA
<213> ORGANISM: Homo sapiens

<400> SEQUENCE: 9
tgacttccag agggatgagc                                              20

<210> SEQ ID NO 10
<211> LENGTH: 21
<212> TYPE: DNA
<213> ORGANISM: Homo sapiens

<400> SEQUENCE: 10
tccaaacaca gcctagtcac c                                            21

<210> SEQ ID NO 11
<211> LENGTH: 20
<212> TYPE: DNA
<213> ORGANISM: Homo sapiens

<400> SEQUENCE: 11
gccctttctg accaagctgt                                              20

<210> SEQ ID NO 12
<211> LENGTH: 20
<212> TYPE: DNA
<213> ORGANISM: Homo sapiens

<400> SEQUENCE: 12
agaagccgaa gaatcccagt                                              20

<210> SEQ ID NO 13
<211> LENGTH: 24
<212> TYPE: DNA
<213> ORGANISM: Homo sapiens

<400> SEQUENCE: 13
atgaaatgtt tggtatgttg acca                                         24

<210> SEQ ID NO 14
<211> LENGTH: 20
<212> TYPE: DNA
<213> ORGANISM: Homo sapiens

<400> SEQUENCE: 14
gtcgtaccca atgtccgagt                                              20

<210> SEQ ID NO 15
<211> LENGTH: 23
<212> TYPE: DNA
<213> ORGANISM: Homo sapiens

<400> SEQUENCE: 15
caggagaaat ttccattttt caa                                          23

<210> SEQ ID NO 16
<211> LENGTH: 24
<212> TYPE: DNA
```

```
<213> ORGANISM: Homo sapiens

<400> SEQUENCE: 16
agaataaagc cttcttcaaa tgag                                          24

<210> SEQ ID NO 17
<211> LENGTH: 20
<212> TYPE: DNA
<213> ORGANISM: Homo sapiens

<400> SEQUENCE: 17
ggccattgtt gcagtttctt                                               20

<210> SEQ ID NO 18
<211> LENGTH: 24
<212> TYPE: DNA
<213> ORGANISM: Homo sapiens

<400> SEQUENCE: 18
cctaggaaaa agaaggaaga gaga                                          24

<210> SEQ ID NO 19
<211> LENGTH: 20
<212> TYPE: DNA
<213> ORGANISM: Homo sapiens

<400> SEQUENCE: 19
acctgcttgc tgtggaattt                                               20

<210> SEQ ID NO 20
<211> LENGTH: 20
<212> TYPE: DNA
<213> ORGANISM: Homo sapiens

<400> SEQUENCE: 20
aggctcctct ctgcctgtct                                               20

<210> SEQ ID NO 21
<211> LENGTH: 20
<212> TYPE: DNA
<213> ORGANISM: Homo sapiens

<400> SEQUENCE: 21
cctggtgtgc tcatttcaga                                               20

<210> SEQ ID NO 22
<211> LENGTH: 24
<212> TYPE: DNA
<213> ORGANISM: Homo sapiens

<400> SEQUENCE: 22
tttttcacct taaaatacca ccaa                                          24

<210> SEQ ID NO 23
<211> LENGTH: 22
<212> TYPE: DNA
<213> ORGANISM: Homo sapiens

<400> SEQUENCE: 23 ggcctttat attcgacatg ga                                             22

<210> SEQ ID NO 24
<211> LENGTH: 21
```

```
<212> TYPE: DNA
<213> ORGANISM: Homo sapiens

<400> SEQUENCE: 24
gcacaggtta cacgttgtgt c                                         21

<210> SEQ ID NO 25
<211> LENGTH: 25
<212> TYPE: DNA
<213> ORGANISM: Homo sapiens

<400> SEQUENCE: 25
ttttcactct aaactgttct gtcca                                     25

<210> SEQ ID NO 26
<211> LENGTH: 20
<212> TYPE: DNA
<213> ORGANISM: Homo sapiens

<400> SEQUENCE: 26
tagtgggagt ggcttcttgg                                           20

<210> SEQ ID NO 27
<211> LENGTH: 20
<212> TYPE: DNA
<213> ORGANISM: Homo sapiens

<400> SEQUENCE: 27
tccacctgcc tgttaggaac                                           20

<210> SEQ ID NO 28
<211> LENGTH: 20
<212> TYPE: DNA
<213> ORGANISM: Homo sapiens

<400> SEQUENCE: 28
atgtgatgtg tccagctcgt                                           20

<210> SEQ ID NO 29
<211> LENGTH: 26
<212> TYPE: DNA
<213> ORGANISM: Homo sapiens

<400> SEQUENCE: 29
ggagtctgct cttctttact ttaagc                                    26

<210> SEQ ID NO 30
<211> LENGTH: 20
<212> TYPE: DNA
<213> ORGANISM: Homo sapiens

<400> SEQUENCE: 30
ggcactgaga acgaaggtaa                                           20

<210> SEQ ID NO 31
<211> LENGTH: 21
<212> TYPE: DNA
<213> ORGANISM: Homo sapiens

<400> SEQUENCE: 31
cgcagacata tacaggccat a                                         21

<210> SEQ ID NO 32
```

```
<211> LENGTH: 19
<212> TYPE: DNA
<213> ORGANISM: Homo sapiens

<400> SEQUENCE: 32
cgtctgtcgt gcatgttga                                                  19

<210> SEQ ID NO 33
<211> LENGTH: 22
<212> TYPE: DNA
<213> ORGANISM: Homo sapiens

<400> SEQUENCE: 33
ccactctctt cttcattctg ga                                              22

<210> SEQ ID NO 34
<211> LENGTH: 25
<212> TYPE: DNA
<213> ORGANISM: Homo sapiens

<400> SEQUENCE: 34
caggaaactt ctcttatggt tcttc                                           25

<210> SEQ ID NO 35
<211> LENGTH: 18
<212> TYPE: DNA
<213> ORGANISM: Homo sapiens

<400> SEQUENCE: 35
gggagcagcg taccattg                                                   18

<210> SEQ ID NO 36
<211> LENGTH: 19
<212> TYPE: DNA
<213> ORGANISM: Homo sapiens

<400> SEQUENCE: 36
ccctgctccc agaaacaac                                                  19

<210> SEQ ID NO 37
<211> LENGTH: 20
<212> TYPE: DNA
<213> ORGANISM: Homo sapiens

<400> SEQUENCE: 37
ggatgagctg gcctcttttt                                                 20

<210> SEQ ID NO 38
<211> LENGTH: 20
<212> TYPE: DNA
<213> ORGANISM: Homo sapiens

<400> SEQUENCE: 38
atgtggaaca atgccactga                                                 20

<210> SEQ ID NO 39
<211> LENGTH: 20
<212> TYPE: DNA
<213> ORGANISM: Homo sapiens

<400> SEQUENCE: 39
tgtggcagga gacagttcag                                                 20
```

```
<210> SEQ ID NO 40
<211> LENGTH: 19
<212> TYPE: DNA
<213> ORGANISM: Homo sapiens

<400> SEQUENCE: 40
cgtagagggc ctccagctt                                              19

<210> SEQ ID NO 41
<211> LENGTH: 23
<212> TYPE: DNA
<213> ORGANISM: Homo sapiens

<400> SEQUENCE: 41
ccacatgatt agcatttgt agc                                          23

<210> SEQ ID NO 42
<211> LENGTH: 21
<212> TYPE: DNA
<213> ORGANISM: Homo sapiens

<400> SEQUENCE: 42
tgtccgagtt tattggtcct t                                           21

<210> SEQ ID NO 43
<211> LENGTH: 27
<212> TYPE: DNA
<213> ORGANISM: Homo sapiens

<400> SEQUENCE: 43
aaaatatgcc ttgtatttca tattcat                                     27

<210> SEQ ID NO 44
<211> LENGTH: 24
<212> TYPE: DNA
<213> ORGANISM: Homo sapiens

<400> SEQUENCE: 44
agaataaagc cttcttcaaa tgag                                        24

<210> SEQ ID NO 45
<211> LENGTH: 21
<212> TYPE: DNA
<213> ORGANISM: Homo sapiens

<400> SEQUENCE: 45
ttctttgtgc ttttcctgga g                                           21

<210> SEQ ID NO 46
<211> LENGTH: 22
<212> TYPE: DNA
<213> ORGANISM: Homo sapiens

<400> SEQUENCE: 46
gctgtaaatg gcaattagat ca                                          22

<210> SEQ ID NO 47
<211> LENGTH: 21
<212> TYPE: DNA
<213> ORGANISM: Homo sapiens

<400> SEQUENCE: 47
ttgggttatg tcaacatgca g                                           21
```

```
<210> SEQ ID NO 48
<211> LENGTH: 23
<212> TYPE: DNA
<213> ORGANISM: Homo sapiens

<400> SEQUENCE: 48
tctctgcctg tcttattcag ctc                                           23

<210> SEQ ID NO 49
<211> LENGTH: 19
<212> TYPE: DNA
<213> ORGANISM: Homo sapiens

<400> SEQUENCE: 49
gctgcttgct gttttctgc                                                19

<210> SEQ ID NO 50
<211> LENGTH: 23
<212> TYPE: DNA
<213> ORGANISM: Homo sapiens

<400> SEQUENCE: 50
cagtctatca aagcatgttc agg                                           23

<210> SEQ ID NO 51
<211> LENGTH: 20
<212> TYPE: DNA
<213> ORGANISM: Homo sapiens

<400> SEQUENCE: 51
tctcacccac agaggctttt                                               20

<210> SEQ ID NO 52
<211> LENGTH: 22
<212> TYPE: DNA
<213> ORGANISM: Homo sapiens

<400> SEQUENCE: 52
gatttcacag ttccctctgc tt                                            22

<210> SEQ ID NO 53
<211> LENGTH: 19
<212> TYPE: DNA
<213> ORGANISM: Homo sapiens

<400> SEQUENCE: 53
cacattttgg cagctggtg                                                19

<210> SEQ ID NO 54
<211> LENGTH: 20
<212> TYPE: DNA
<213> ORGANISM: Homo sapiens

<400> SEQUENCE: 54
gcatggagag cacctgaatc                                               20

<210> SEQ ID NO 55
<211> LENGTH: 26
<212> TYPE: DNA
<213> ORGANISM: Homo sapiens

<400> SEQUENCE: 55
ggaaccaatt ttaatgataa actcaa                                        26
```

<210> SEQ ID NO 56
<211> LENGTH: 19
<212> TYPE: DNA
<213> ORGANISM: Homo sapiens

<400> SEQUENCE: 56
cgtccagctc caggatgat                                                    19

<210> SEQ ID NO 57
<211> LENGTH: 22
<212> TYPE: DNA
<213> ORGANISM: Homo sapiens

<400> SEQUENCE: 57
gagctgtctt ttgtactctg ct                                                22

<210> SEQ ID NO 58
<211> LENGTH: 23
<212> TYPE: DNA
<213> ORGANISM: Homo sapiens

<400> SEQUENCE: 58
cagcgttaat attgtccatt tca                                               23

<210> SEQ ID NO 59
<211> LENGTH: 22
<212> TYPE: DNA
<213> ORGANISM: Homo sapiens

<400> SEQUENCE: 59
ggatctaaat gggtgggtaa ag                                                22

<210> SEQ ID NO 60
<211> LENGTH: 19
<212> TYPE: DNA
<213> ORGANISM: Homo sapiens

<400> SEQUENCE: 60
gggcatgaga ctgcaggag                                                    19

<210> SEQ ID NO 61
<211> LENGTH: 20
<212> TYPE: DNA
<213> ORGANISM: Homo sapiens

<400> SEQUENCE: 61
ttcttggaca gcttttccag                                                   20

<210> SEQ ID NO 62
<211> LENGTH: 18
<212> TYPE: DNA
<213> ORGANISM: Homo sapiens

<400> SEQUENCE: 62
cctccagctt gccgtcac                                                     18

<210> SEQ ID NO 63
<211> LENGTH: 22
<212> TYPE: DNA
<213> ORGANISM: Homo sapiens

<400> SEQUENCE: 63
tgtccgagtt tattggtcct ta                                    22

<210> SEQ ID NO 64
<211> LENGTH: 25
<212> TYPE: DNA
<213> ORGANISM: Homo sapiens

<400> SEQUENCE: 64
gagaaatgca gttttctatg atgaa                                 25

<210> SEQ ID NO 65
<211> LENGTH: 20
<212> TYPE: DNA
<213> ORGANISM: Homo sapiens

<400> SEQUENCE: 65
tttgtgcttt tcctggaggt                                       20

<210> SEQ ID NO 66
<211> LENGTH: 23
<212> TYPE: DNA
<213> ORGANISM: Homo sapiens

<400> SEQUENCE: 66
gccagtagag aggctaagtg tca                                   23

<210> SEQ ID NO 67
<211> LENGTH: 23
<212> TYPE: DNA
<213> ORGANISM: Homo sapiens

<400> SEQUENCE: 67
aagcatgttc aggtatcctc ttc                                   23

<210> SEQ ID NO 68
<211> LENGTH: 18
<212> TYPE: DNA
<213> ORGANISM: Homo sapiens

<400> SEQUENCE: 68
cacagaggct ttttggca                                         18

<210> SEQ ID NO 69
<211> LENGTH: 25
<212> TYPE: DNA
<213> ORGANISM: Homo sapiens

<400> SEQUENCE: 69
tttgttcact acaagtccct taaaa                                 25

<210> SEQ ID NO 70
<211> LENGTH: 22
<212> TYPE: DNA
<213> ORGANISM: Homo sapiens

<400> SEQUENCE: 70
gataaactca aggatggcat ct                                    22

<210> SEQ ID NO 71
<211> LENGTH: 22
<212> TYPE: DNA
<213> ORGANISM: Homo sapiens
<220> FEATURE:
<221> NAME/KEY: misc_feature

```
<222> LOCATION: (11)..(16)
<223> OTHER INFORMATION: n is a, c, g, or t

<400> SEQUENCE: 71
ccgactcgag nnnnnnatgt gg                                              22

<210> SEQ ID NO 72
<211> LENGTH: 22
<212> TYPE: DNA
<213> ORGANISM: Homo sapiens
<220> FEATURE:
<221> NAME/KEY: misc_feature
<222> LOCATION: (11)..(16)
<223> OTHER INFORMATION: n is a, c, g, or t

<400> SEQUENCE: 72
ccgactcgag nnnnnnatca tc                                              22

<210> SEQ ID NO 73
<211> LENGTH: 22
<212> TYPE: DNA
<213> ORGANISM: Homo sapiens
<220> FEATURE:
<221> NAME/KEY: misc_feature
<222> LOCATION: (11)..(16)
<223> OTHER INFORMATION: n is a, c, g, or t

<400> SEQUENCE: 73
ccgactcgag nnnnnnttga gg                                              22

<210> SEQ ID NO 74
<211> LENGTH: 22
<212> TYPE: DNA
<213> ORGANISM: Homo sapiens
<220> FEATURE:
<221> NAME/KEY: misc_feature
<222> LOCATION: (11)..(16)
<223> OTHER INFORMATION: n is a, c, g, or t

<400> SEQUENCE: 74
ccgactcgag nnnnnngata ca                                              22

<210> SEQ ID NO 75
<211> LENGTH: 22
<212> TYPE: DNA
<213> ORGANISM: Homo sapiens
<220> FEATURE:
<221> NAME/KEY: misc_feature
<222> LOCATION: (11)..(16)
<223> OTHER INFORMATION: n is a, c, g, or t

<400> SEQUENCE: 75
ccgactcgag nnnnnnatgt gg                                              22
```

MICRODISSECTION-BASED METHODS FOR DETERMINING GENOMIC FEATURES OF SINGLE CHROMOSOMES

FIELD OF THE INVENTION

This invention relates generally to the identification and characterization of genomic features of chromosomes. More specifically, the present invention is directed to microdissection-based methods that facilitate direct determination of genomic features of either normal or abnormal single chromosomes.

BACKGROUND OF THE INVENTION

Chromosome aberration is a hallmark of cancer, which provides valuable clues to pinpoint the candidates for cancer-related genes. Cancer-specific chromosome aberrations often result in alterations in the structure and/or the dosage of cancer-causing genes [Balmain, et al. *Nat. Genet.* 33 Suppl: 238-244 (2003)]. Examples include Bcr/Abl fusion gene caused by the translocation between chromosomes 9 and 22 (Philadelphia chromosome) in chronic myeloid leukemia (CML), and loss of a copy of the Rb gene caused by the deletion of the proximal region of the long arm of chromosome 13 in retinoblastoma. Chromosome rearrangement in cancers may also result in alterations in other genes, which may not be the primary cause of cancer, but have an impact on cancer susceptibility and/or cancer progression, and thus have a great value in cancer risk assessment, diagnosis and prognosis. Therefore, genes and their alterations involved in all clonal and recurrent chromosome abnormalities should be carefully characterized.

Most cancer chromosome abnormalities are detected through cancer cytogenetics studies. Once a clonal chromosome structure abnormality is detected, researchers may further define the genomic region(s) involved in the abnormality by FISH or other DNA hybridization-based techniques to "walk through" the abnormality with various cloned genomic sequences. The gene content in the defined region(s) can be disclosed by matching the genes that have been mapped in the regions from the human genome databases. This approach can narrow down the candidates for cancer-related genes, from which the actual cancer-causing and cancer-risk genes may be identified by genotype-phenotype correlation and functional studies. Such a strategy is referred to as cytogenetics-based positional cloning and is so far the most successful strategy for identifying cancer-related genes, particularly from hematological cancers. However, this strategy has limitations.

First, it is heavily relied on in standard chromosome studies and FISH to define the genomic regions that are involved in cancer chromosome aberrations. Due to limited resolution and often poor cancer chromosome morphology, determining the genomic origins of cancer chromosome abnormalities can be particularly difficult. It is often further complicated when the aberrations are only detected in a small number of cancer cells that are mixed with a large population of cells with an apparently normal karyotype. Because of this limitation, the genomic origins of many observed cancer chromosome abnormalities cannot be identified for further analysis.

Second, the cytogenetics-based positional cloning is not a straightforward, high-throughput strategy; the analytical process of this strategy is cumbersome and labor-intensive. It may take several months for a skillful researcher to fully analyze one abnormality to determine the genomic regions, breakpoints and gene content involved in the abnormality. In addition, such an analysis usually requires a significant amount of cancer specimens, but that are not always available. Therefore, only a very small fraction of observed cancer chromosome abnormalities have been thoroughly characterized for positional cloning. Linkage analysis can also be used to reveal candidate loci for positional cloning. However, this method is more commonly used for studying constitutional Mendelian diseases and rare familial cancer cases; its application seems to be limited in genetic analysis of sporadic cancers, perhaps due to the complexity of the cancer genetics and genomics.

Genome-wide screening for genomic DNA copy number imbalance is another strategy for cancer genetic analysis, including restriction landmark genome scanning [Hayashizaki, et al., *Electrophoresis* 14: 251-258 m(1993)], comparative genomic hybridization (CGH) [Kallioniemi, et al. *Science* 258: 818-821 (1992)], high-throughput quantitative PCR [Ginzinger, et al. *Cancer Res.* 60: 5405-5409 (2000)] and molecular subtraction techniques, such as representational display analysis [Lisitsyn, et al. *Science* 259: 946-951 (1993)]. These global screening techniques, particularly the array-based CGH [Albertson, et al., *Nat. Genet.* 25: 144-146 (2000)], are powerful tools to detect genome-wide DNA sequence dosage change, including deletion and duplication, in the cancer genome. However, these techniques also have limitations. They usually cannot detect balanced chromosomal rearrangements that often result in cancer-causing gene fusion and/or breaking apart, such as the Bcr/Abl fusion gene in CML and the MLL gene split in various types of leukemia. In addition, the capability of these techniques to detect DNA copy number imbalance can be complicated or impaired in mixed cell populations. Unfortunately, most cancer specimens are contaminated with more or less normal cells, and genomic changes in most cancers are heterogeneous; cancer tissues are often mixed with multiple cell lines with multiple clonal and/or non-clonal (random) genomic abnormalities. Furthermore, these techniques may not directly reveal the dosage of individual genes involved in the unbalanced genomic regions. For example, the resolution of the current array CGH is about a hundred thousand base pairs of genomic DNA [Albertson, et al., *Nat. Genet.* 25: 144-146 (2000); Vissers, et al., *Am. J: Hum. Genet.* 73: 1261-1270 (2003).], which is better than that of the cytogenetic analysis, but is not enough to determine the dosage alterations in individual genes. Array-based gene expression analysis is also a powerful tool for cancer studies, which reveals expression patterns of all known or predicted genes in cancers [Hanash, S. *Nat. Rev. Cancer* 4: 638-644 (2004)]. The expression level of each gene can be measured and genes with similar expression levels or with similar functions can be grouped for further analysis. Since many genes may show a similar expression level and the abnormal expression may or may not represent the primary genetic change in cancer, the array expression analysis is an excellent tool for cancer biology studies rather than identification of cancer-causing genes and primary genetic changes. From a technical point of view, the best way to characterize a chromosome rearrangement is directly analyzing the genomic DNA from the abnormal chromosome, which increases the efficiency and accuracy of detecting the genomic content, gene content and possible mutations involved in the regions. As of yet, however, most current technical strategies do not have the ability to directly characterize detectable chromosome aberrations.

In addition, none of the techniques described above can directly uncover the genomic features, such as DNA sequence variations, of the abnormal chromosome regions. Such information is an important part of molecular profile of cancer, which will facilitate cancer epidemiology studies, risk assessment, diagnosis and prognosis. Genomic sequence variation or polymorphism is an important feature of the genome. The most common type of variation is single nucleotide polymorphism (SNP) that is defined as a single nucleotide variation at a locus with the frequency of the minor allele greater than 1% in at least one population [Risch, N. J. *Nature* 405: 847-856 (2000).]. It is estimated that the human genome contains more than 15 million SNPs [Botstein, et al. *Nat. Genet.* 33 Suppl: 228-237 (2003)]. These polymorphisms are valuable markers for genetic association studies, because they are frequently linked with disease-related genes or traits. It is apparent that SNPs are not inherited randomly in the same chromosome; instead, they are often inherited as phased combinations of specific alleles in particular populations. Therefore, analyzing phased SNPs or SNP haplotypes provides a more informative approach to study genetic associations.

In general, haplotype is a combination of linked polymorphic alleles on a single chromosome. A given homologous chromosome pair in the diploid genome has two haplotypes, representing maternal and paternal origins [The International HapMap Consortium. *Nature* 426, 789-796 (2003)]. Haplotypes of the human genome appear to be organized as discrete blocks with an average size of 9-18 kb in length (ranging from less than 1 kb to more than 170 kb) due to linkage disequilibrium (LD) [Gabriel, S. B. et al. *Science* 296, 2225-2229 (2002)]. Linked polymorphic alleles within each block tend to act as a single multi-site allele with limited haplotype diversity [Wall, J. D. & Pritchard J. K. *Nat. Rev. Genet.* 4, 587-597 (2003)]. The haplotype blocks represent the evolution, inheritance and recombination histories of the genome. Thus, analyzing haplotype blocks of highly condensed polymorphic markers, such as SNPs, provides a powerful tool for genetic association studies [Bostein, D. & Risch, N. *Nat. Genet. Suppl.* 33, 228-237 (2003); Crawford, D. C. et al. *Am. J. Hum. Genet.* 74, 610-622 (2004); Drysdale, C. M. et al. *Proc. Natl. Acad. Sci. USA* 97, 10483-10488 (2000)]. Uncovering SNP haplotypes of the abnormal chromosome regions in cancer should also be of great help for tracing the origins of the abnormal alleles, following-up the progression of the abnormalities, identifying low-penetrance cancer-related traits, and studying drug response and prognosis.

However, unambiguously determining haplotypes of SNP blocks, especially large blocks, is particularly challenging due to technical limitations. There have been two broad categories of tools for unambiguous haplotyping: genotyping family pedigrees and directly genotyping SNPs on a single chromosome of interest [Crawford, D. C. & Nickerson, D. A. *Annu. Rev. Med.* 56, 303-320 (2005)]. The former is expensive, time-consuming and requires DNA samples from several generations, which are not always available. In addition, accurately assigning SNP phase using family-based methods becomes increasingly difficult as more loci are considered. Meanwhile, the latter currently relies on enrichment of DNA of single-chromosome origin using complicated methods, such as somatic cell hybrid and multi-step allele-specific PCR, which is also time-consuming and expensive. These limitations make it difficult to apply unambiguous SNP haplotype analysis to either individual- or population-based genetic association studies.

Taken together, effectively identifying disease-causing and disease-risk genes as well as their genomic alterations/variations, particularly from cancer-associated clonal chromosome aberrations and constitutional mosaicism from mixed cell populations, remains a great challenge in genetic research.

SUMMARY OF THE INVENTION

The present invention provides a chromosome microdissection-based strategy for detailed molecular analysis of any cytogenetically visible chromosome regions from a single cell. It is a straightforward "what you see is what you get" approach that possesses several unique advantages. It allows the direct isolation of any normal or abnormal chromosomes or chromosome regions from targeted single cells without the interference of the surrounding cells. The isolated chromosomes or chromosome regions are efficiently amplified for high-resolution genomic analysis, such as determination of the breakpoints, gene content, DNA content and genetic variations of the target regions. This strategy provides a unique tool to analyze clonal acquired abnormalities in cancer cells and mosaic constitutional abnormalities observed in a variety of genetic disorders. In addition, this strategy is particularly useful for unambiguously determining haplotypes of any genomic regions without the requirement of family pedigrees and genotypes, LD and population genomic information, or complicated statistical analysis and computing. For example, it can quickly determine SNP haplotypes of any single or multiple haplotype blocks, chromosome regions or chromosomes regardless their genomic locations and sizes, as well as the frequency of LD in the target regions. Furthermore, this strategy has a strong potential to be used for genome-wide and population-based haplotype analysis when it can be applied with large scale SNP array technologies. Amplified single chromosome DNA samples may be analyzed using SNP arrays or, alternatively, subjected to genotyping by primer extension and DNA sequencing. For the genome-wide analysis, one may separate and amplify haploid chromosome sets of an individual, and directly determine the haplotypes of each haploid set using appropriate SNP arrays. This new strategy may largely facilitate both individual- and population-based genetic association studies. In addition, this strategy may also be applied to haplotype analysis of species other than human.

Accordingly, the present provides in a first embodiment a method of identifying a genomic feature present within a visible chromosome region. Such a method includes steps of: (a) micro-dissecting a single copy of a chromosome to obtain a visible chromosome region; (b) amplifying the visible chromosome region to obtain amplified single chromosome DNA; and (c) subjecting the amplified single chromosome DNA to micro-array analysis whereby such analysis identifies at least one genomic feature present within the visible chromosome region.

In certain embodiments, the method includes the additional step of performing reverse fluorescence in situ hybridization (FISH) on a chromosome preparation using the amplified single chromosome DNA to identify a genomic origin of the visible chromosome region. With this information available, the micro-array analysis may then be at least partially targeted to the genomic origin of the visible chromosome region; knowledge of the genomic origin is particularly valuable where region specific micro-array analysis is performed.

In a preferred embodiment, the genomic feature identified by the method is a single nucleotide polymorphism (SNP). If a plurality of single nucleotide polymorphisms (SNPs) are identified, then a SNP haplotype of the visible chromosome region is provided by the method. As well, where the method is repeated using a corresponding haploid chromosome homologue, then SNP haplotypes of a chromosome homologue set are provided by the method.

In certain embodiments, the visible chromosome region comprises a visible aberration. The chromosome microdissected in the method is preferably obtained from a single cell, most preferably isolated from a population of heterogeneous cells of human origin. The chromosome region carrying an aberration can be amplified and characterized by high-resolution genomic DNA arrays for determining the breakpoints, gene content and DNA content which are involved in the aberration. While the characterization of abnormal chromosomes is a preferred application of the present invention, it should be understood that the invention is equally applicable to the characterization of genomic features in normal chromosomes of human or non-human origin.

Other objects, features and advantages of the present invention will become apparent after review of the specification, claims and drawings.

DETAILED DESCRIPTION OF THE INVENTION

I. In General

Figure 1:
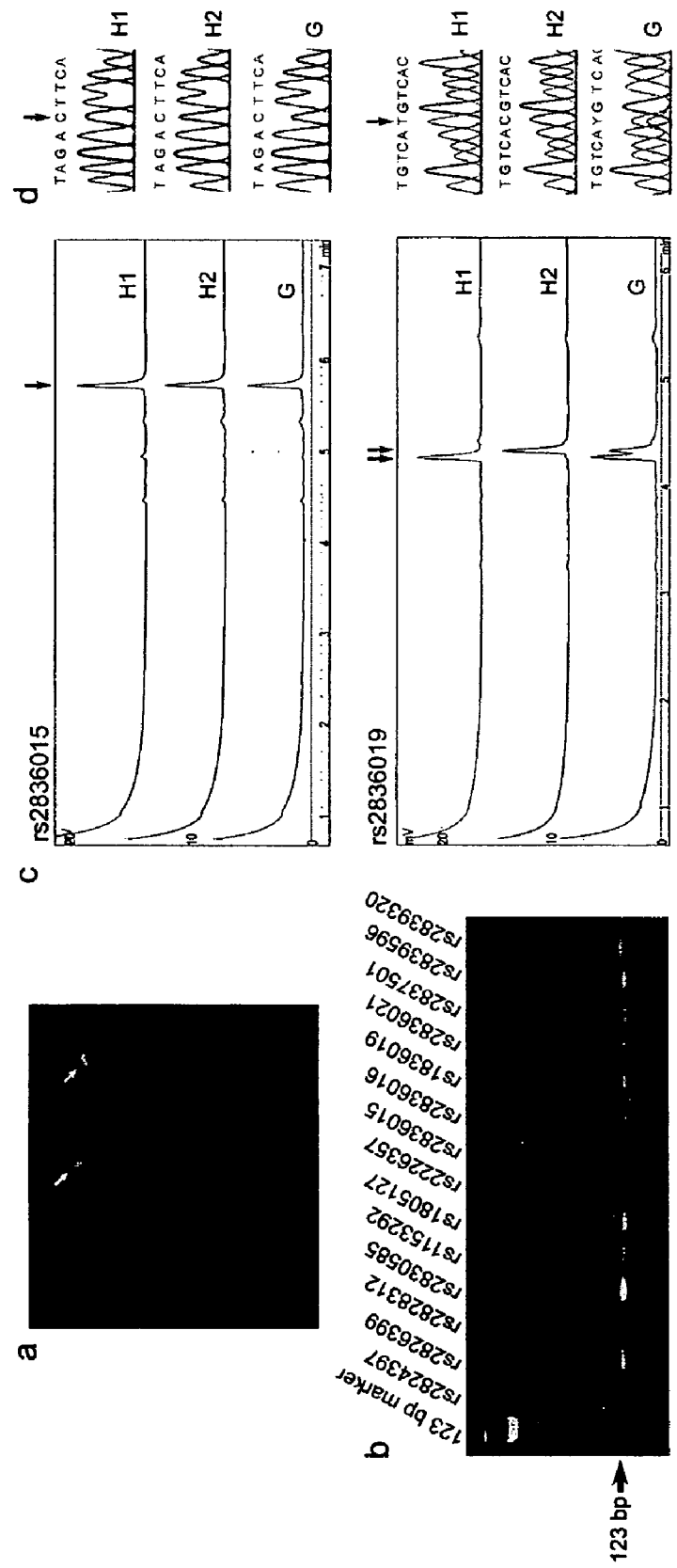
FIG. 1. Evaluation of microdissection and amplification of single-copy 21q and determining of SNP alleles on single 21qs. (a) Evaluation by FISH. Fluorescence-labeled DNA amplified from a single 21q hybridizes exclusively back to the 21qs with strong and even hybridization signals (arrows). (b) Evaluation by locus-specific PCR. The gel photography demonstrates all 14 tested alleles that are amplified from a single 21q. (c) Testing of SNP alleles at each locus by primer extension as described in Example 1. Arrows indicate the allele peaks. The homozygous locus rs2836015 shows only an identical single allele peak in each 21q homologue and in the genomic DNA; while the heterozygous locus rs2836019 shows a different single peak in each homologue and both peaks in the genomic DNA. (d) Determining of SNP alleles by DNA sequencing. Each amplified allele is also sequenced using ABI 3700 DNA analytical system. The arrows indicate the corresponding SNPs in the same samples tested in (c). H-homologue sample; G-genomic DNA.

Before the present materials methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

II. The Invention

The present invention provides a strategy that can readily and reliability characterize genomic features contained within a visible chromosome region of a single chromosome. The invention is particularly well-suited in certain embodiments to characterize visible chromosome aberrations present in, for example, cancer cells. In the abnormal chromosome context, the present technology facilitates the identification of genes and their genomic changes and/or polymorphisms (e.g., haplotype blocks) associated with chromosomal aberrations. In other embodiments, the present technology is equally suited to characterize normal chromosomes, including the identification of SNP alleles for haplotyping a specific chromosome or, alternatively, an entire genome.

Visible chromosome regions, no matter whether their genomic origins are identified or not, are characterized according to the invention by: 1) isolating chromosome regions using chromosome microdissection; 2) amplifyng the regions from single copies of chromosomes; and 3) subjecting the amplified single chromosome DNA to high-resolution genomic/gene arrays in order to determine a genomic feature including, but not limited to, DNA polymorphisms, genomic intervals, breakpoint locations and the gene content. In more preferred embodiments, methods according to the invention identify SNP alleles present within the visible chromosome region thusly providing the direct determination of a single chromosome's haplotype.

In terms of analyzing abnormal chromosomes, particularly those associated with cancer cells, this strategy has unique advantages that will overcome current technical difficulties, and greatly facilitate the effort of understanding cancer genomics and genetics. First, any visible chromosome aberration can be quickly and precisely isolate by microdissection. Where aberrant morphologies are concerned, the genomic origin of the aberration can also be quickly and precisely determined by reverse FISH. Limited number of abnormal cells in a mixed cell population and poor cancer chromosome morphology will not affect the analysis, since as low as only one copy of the abnormal region is needed for dissection and the genomic origins of the abnormalities will be determined on normal chromosomes by FISH using dissected DNA as probes. Second, the abnormal region-specific high-resolution genomic/gene array analysis using the dissected DNA will be much more efficient and accurate than the traditional positional cloning on determining the genomic and gene content of abnormal regions. Third, this strategy allows the direct determine of SNP alleles on a single copy of abnormal chromosome, which represent the haplotype of the chromosome. Since the abnormal DNA is isolated, other genomic alterations and variations in the abnormal region may also be directly analyzed. This feature has a particular significance on cancer genetic research, which makes it possible to directly identify molecular characteristics or the molecular basis (the genomic profile) of the genomic regions that are involved in cancer-related abnormalities in each individual cancer patient. Such molecular basis and profiles will largely facilitate the identification of genetic factors that influence the genome stability and the individuals' risk of developing cancer or their ability of responding to the cancer therapy. Fourth, this strategy can characterize virtually any type of chromosome abnormalities from any dividing cell populations, mixed or not mixed, once the abnormalities are detected by cytogenetics.

Distinct from most of the current strategies, this is the first "what you can see, is what you can analyze" strategy, which will allow cancer researchers to maximally utilize the cancer cytogenetic findings for identifying cancer-related genes, genomic alterations and variations. This straightforward and efficient technical strategy makes it possible to systematically analyze all detectable cancer abnormalities. Of course, the application of the present invention is applicable to genome-wide genomic analysis for both normal and abnormal cell types (e.g., directly measuring the haplotypes of an entire genome).

The present invention combines techniques including microdissection, DNA amplification and DNA array techniques. Such techniques and their application to the present invention are further described below.

Chromosome microdissection is a unique technique of isolating chromosomes or chromosome regions from animal and plant cells by physically removing the regions of interest from the chromosome preparations using a sharp needle that is controlled by a micromanipulator or a laser bean [e.g., Kao, et al., *BioEssays* 15: 141-146 (1993); Kao, F. T. In Methods of genome analysis in plants (edited by Jauhar, P P), *CRC Press*, New York, pp 329-343 (1996)]. Dissected chromosome regions have been amplified by various PCR-based techniques [e.g., see Kao, F. T (1996), ibid] and by Multiple Displacement Amplification (MDA) for a variety of basic research and clinical applications, including construction of region-specific genomic libraries for genomic analysis, cloning of disease genes, generation of region-specific FISH probes and identification of the genomic origins of chromosome abnormalities. A unique and powerful feature that makes this technique superior than others is its capability of isolating and cloning any cytogenetically visible chromosome regions from as few as a single metaphase cell from any eukaryotic species.

The amplification of dissected DNA is a key step in the present invention. Linker adaptor-based and degenerate oligonucleotide primer (DOP)-based PCR techniques are known in the field and may be adapted, as described herein, for use in the present invention. DNA amplified by such techniques has been successfully used for constructing genomic libraries and generating FISH probes [e.g., see Kao, F. T (1996), ibid]. Multiple Displacement Amplification (MDA) is a relatively-new technology for genomic DNA amplification using a special DNA polymerase, phi29 polymerase, which is isolated from the phage phi-29 strain [Dean, et al, *Proc. Natl. Acad. Sci. U.S.A.* 99: 5261-5266.16-18; (2002); Hosono, et al., *Genome Res.* 13: 954-964 (2003); . Barker, et al., *Genome Res.* 14: 901-907 (2004)]. This enzyme can efficiently amplify a trace amount of DNA templates in 30° C. by continuously replacing one parent DNA chain with a new synthesized one without changing the reaction temperature. Another unique feature of phi29 DNA polymerase is that it amplifies large molecules, up to a few hundred kb, and the amplification appears to be more complete and more even. While microdissected DNA has been amplified using the techniques described, it is of particular note that amplified DNA samples from microdissection have not been shown amendable to micro-array analysis outside of the present disclosure.

In general, DNA array is a technology that spots a large number of DNA samples in a small surface with a very high density for DNA hybridization analysis [Schena, et al., *Science* 270: 467-470 (1995)]. Using arrays, researchers can examine the full complexity of a genome in a single experiment. Arrays have been applied to studies in gene expression, genome mapping, SNP discrimination, transcription factor activity, toxicity, pathogen identification and detection, as well as many other applications.

In the present invention, at least two different types of arrays find particular utility; SNP array and region-specific high-resolution genomic/gene array. Currently, there are several commercially available SNP array techniques suitable for use in the present invention including, but not limited to, the Affymatrix human SNP array (Genechip Mapping 100K set) that contains over 100,000 SNPs genome-wide [Affymetrix, Inc., http://www.affymetrix-.com/products/arrays/specific/100k.affx]. High-resolution genomic/gene arrays useful in the present invention have been developed and are commercially available from NimbleGen Systems, Inc [Nimblegen System, Inc. illustrative information available at www.nimblegen.com/products/index.html.]. Such high-density microarrays are manufactured via a proprietary Maskless Array Synthesizer (MAS) technology. This technology generates arrays with extremely high inter-array reproducibility (up to $r^2>0.99$) and very low intra-array coefficient of variation (cv<12%) across the array surface. However, the present invention is not limited in the array technology it may incorporate. For example, large genomic clone-based CGH arrays may be utilized to characterize chromosome breakpoints while oligo-based arrays may be used to uncover the detailed gene content in the tested regions.

Various aspects of the invention are described in further detail in the following subsections.

III. EXAMPLES

Example 1

Determining Single Nucleotide Polymorphism (SNP) Haplotypes Using Dissected Single Chromosomes This example describes the unambiguous determination of SNP haplotypes of a selected chromosome region using a technique according to the present invention. The disclosed technique includes the steps of single chromosome microdissection, universal DNA modification, and direct analysis of amplified single-chromosome DNA by primer extension.

The inventors analyzed the haplotypes of 14 SNP loci across the long arm of chromosome 21 (21q) in five normal Caucasians, including three unrelated individuals, a mother and her son. Briefly, the inventors isolated 10 single-copy 21qs from each individual in five cultured metaphase peripheral blood cells by chromosome microdissection and amplified each individual 21q using modified degenerate oligonucleotide primed PCR (DOP-PCR). The quality of the dissection and amplification was evaluated by fluorescence in situ hybridization (FISH), in which, two randomly selected amplified 21qs from each individual were hybridized to normal metaphase cells. All tested samples showed strong and even hybridization signals exclusively on 21q (FIG. 1a), indicating that the dissections were accurate and the single-chromosome amplifications were efficient.

In order to examine the efficiency and coverage of this strategy for haplotype analysis at both individual block and whole chromosome arm levels, the inventors selected 14 21q-specific SNP loci from Human Genome Resource, NCBI (http://www.ncbi.nlm.nih.gov/genome/guide/human) for analysis. These loci span approximately 30 Mb along 21q, including five that are located on a 10 kb DNA stretch within a known haplotype block and nine that are evenly distributed along the rest regions of 21q (FIG. 2) [Patil, N. et al. Science 294, 1719-1723 (2001)]. The SNP alleles were individually amplified from the DOP-PCR products of each 21q using locus-specific primers. On average, about 8.2 (range 6-14) loci were amplified from a single copy of 21q. FIG. 1b shows an example of amplification of all 14 SNP loci from a single 21q. Loss of alleles from a single dissected chromosome is anticipated because of the possibility of random DNA damage during the process. It was demonstrated that alleles lost from a 21q homologue in one cell could be readily amplified from the same homologue in a different cell of the same individual. The tested alleles were also amplified from the genomic DNA of each individual as controls. The inventors then genotyped each 21q and the corresponding control genomic DNA sample using locus-specific primer extension and DNA sequencing. As expected, only a single allele at every locus on single-copy 21qs was detected; whereas, mixed heterozygous alleles were detected at some loci in genomic DNA samples (FIGS. 1c and 1d). Two alleles detected at a genomic heterozygous locus of an individual were always detected separately on two corresponding 21q homologues (FIGS. 1c and 1d). These findings demonstrate that the amplified DNA samples from dissected single chromosomes are also suitable for array analysis, particularly SNP analysis.

Figure 2:
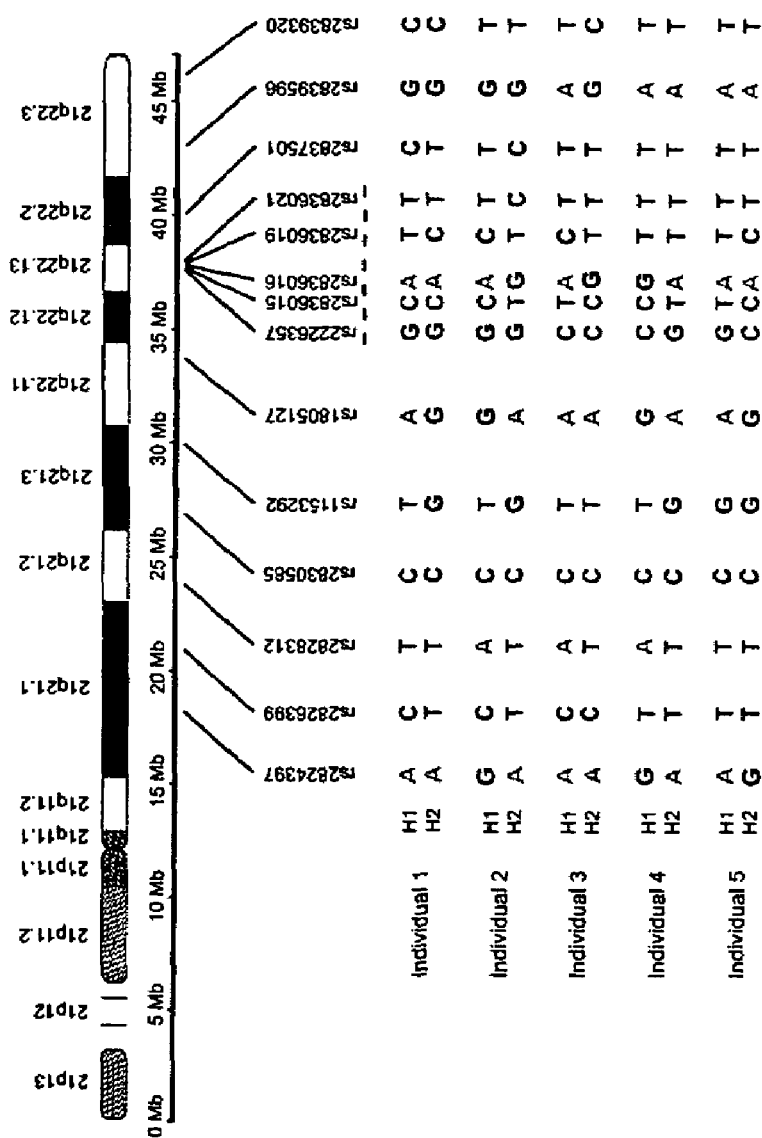
FIG. 2. SNP haplotypes detected in five individuals. The dash line indicates the haplotype block B000966 that was predicted having limited haplotype diversity across different ethnic groups [Patil et al. *Science* 294:1719-1723 (2001)]. Two haplotypes of this block are shared by unrelated individuals (GCACT shared by individuals 1 and 2 and CCGTT shared by individuals 3 and 4). Individual 4 and 5 are mother and son, who share a same haplotype (individual 4-H2 and individual 5-H1), demonstrating that the inheritance of a specific haplotype between generations can also be readily analyzed by the present invention.
Figure 3:
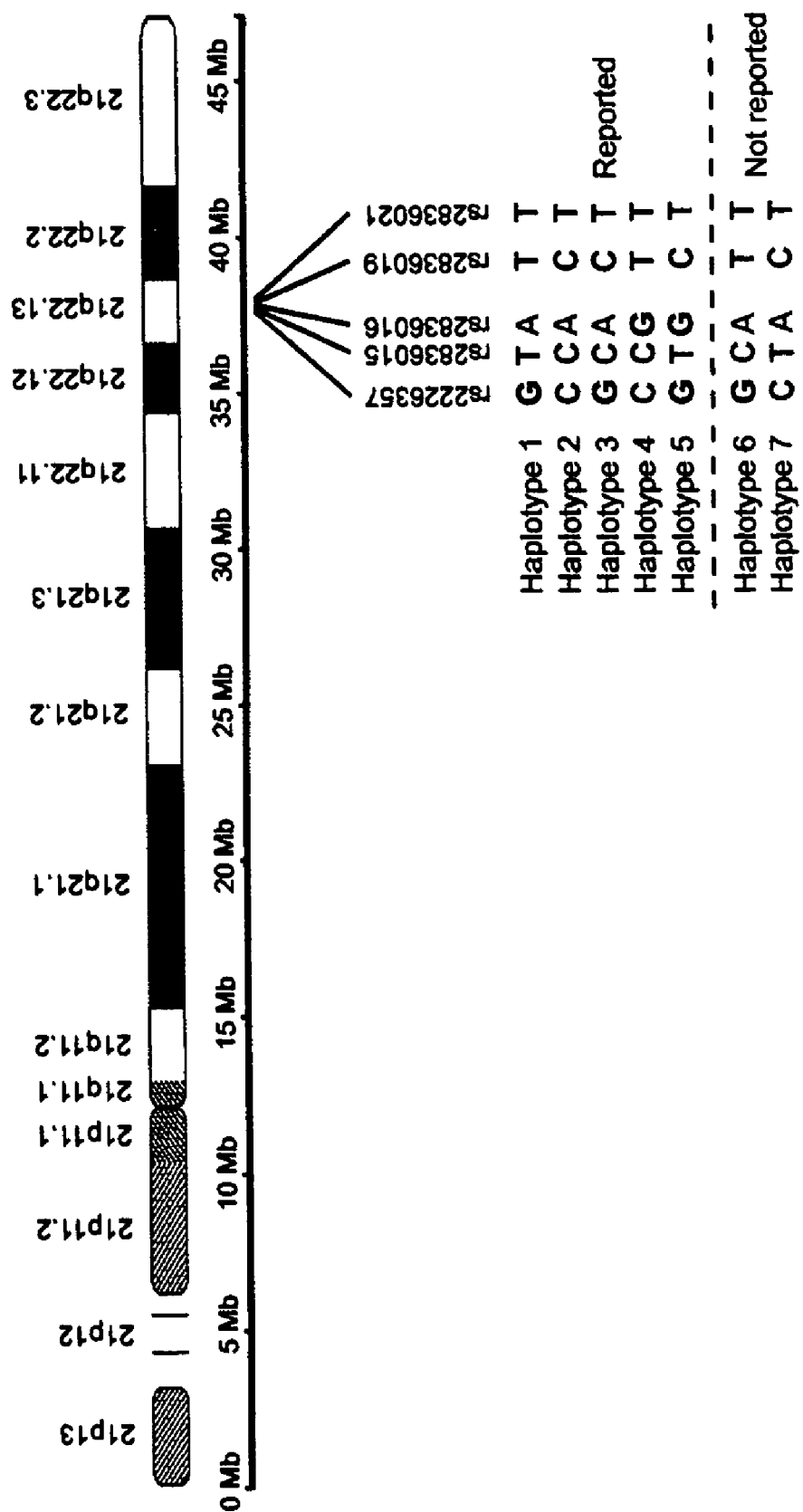
FIG. 3. Several different haplotypes of Haplotype Block B000966 determined in a group of 5 individuals, including 5 reported and 2 unreported haplotypes.

Most importantly, the SNP haplotype of a 21q homologue was automatically uncovered once the SNP polymorphic alleles on that homologue were determined. In the present study, 3-5 metaphase cells from an individual were sufficient for a full haplotype analysis of the 14 loci; when partial loss of alleles occurs on a single chromosome, the complete haplotype of the chromosome can always be determined by comparing allele phases in a few different cells. Using this strategy, the inventors unambiguously determined the haplotype of the 14 loci on each 21q homologue from the five tested individuals (FIG. 2). At least two of the haplotypes determined for Haplotype Block B000966 were unreported thereby further demonstrating the present invention's utility in the identification of genomic features (FIG. 3).

Materials and methods related to this example are as follows:

Microdissection and DOP-PCR

Metaphase chromosomes for microdissection were prepared on 24×50 mm coverslips as previously described [Kao, F. T. and Yu, J. W. *Proc. Natl. Acad. Sci. USA* 88, 1844-1848 (1991)]. Single chromosome microdissection and universal amplification was modified from previously published methods [Meltzer, P. S. et al. *Nat. Genet.* 1, 24-28 (1992); Jordan, B. et al. *Proc. Natl. Acad. Sci. USA* 99, 2942-2947 (2002)]. Briefly, a single 21q was dissected with a sharp glass needle using TransferMan NK2 micromanipulator (Eppendorf) attached to the microscope, and transferred to 5 µl collection buffer containing 5 mM NaCl, 2 mM MgCl$_2$, 4 mM Tris-Cl (pH7.5), 200 µM dNTPs and 1 µM equally mixed four degenerate primers (5'-CCGACTCGAGNNNNNNATGTGG-3' (SEQ ID NO:71), 5'-CCGACTCGAGNNNNNNATCATC-3' (SEQ ID NO:72), 5'-CCGACTCGAGNNNNNNTTGAGG-3' (SEQ ID NO:73) and 5'-CCGACTCGAGNNNNNNGATACA-3' (SEQ ID NO:74)). The dissected 21q was then treated with 1U Topoisomerase I (Promega) at 37° C. for 20 min, denatured at 96° C. for 10 min and followed by eight cycles of pre-amplification using 1:8 freshly diluted Sequenase Version 2.0 DNA polymerase (USB). Each cycle includes 94° C. 1 min, 30° C. 2 min, 37° C. 2 min and addition of 0.2U fresh enzyme. The pre-amplification product was further amplified by PCR in 50 µl reaction solution containing 2U Taq DNA polymerase (Eppendorf), 1×PCR buffer with 1.5 mM MgCl$_2$ (Eppendorf), 100 µM dNTPs and 0.2 µM mixed degenerate primers. The PCR cycles include a hot start at 94° C. for 3 min, 35 cycles of 94° C. 1 min, 56° C. 1 min and 72° C. 2 min, and a final extension at 72° C. for 10 min. The PCR products were examined by electrophoresis on 1% agarose gel.

Fluorescent in Situ Hybridization (FISH)

The DOP-PCR products were labeled with Digoxigenin-11-dUTP (Roche) and hybridized to spreads of human metaphase chromosomes according to Non-Radioactive In Situ Hybridization Application Manual (Roche, see, e.g., www.roche-applied-science.com/PROD_INF/MANUALS/). FISH results were analyzed and documented using the proprietary Cytovision system available from Applied Imaging.

Isolation of Genomic DNA

Genomic DNA from each tested individual was isolated from blood cells using the Wizard Genomic DNA Purification Kit (Promega).

solution (50 µl for each PCR reaction) contains 1 mM $MgCl_2$, 100 µM dNTPs, 0.2 µM of each forward and reverse primers, 1×PCR buffer and 2U Taq DNA polymerase (Eppendorf). The PCR products were examined on 3% agarose gel and treated with Exonuclease I and Shrimp Alkaline Phosphatase (ExoSAP-IT, USB) to clean up unincorporated primers and dNTPs for the following primer extension and sequencing analyses.

TABLE 1

Chromosome 21q SNP locus-specific PCR primers

| refSNP ID | Starting primer (5'→3') (SEQ ID NO) | Nest primer (5'→3') (SEQ ID NO) |
| --- | --- | --- |
| rs2824397 | GCCAGGGCATGTTTTATAGG (1)<br>CCACTGTTTTGGCACTGAGA (2) | GGAGTCTGCTCTTCTTTACTTTAAGC (29)<br>GGCACTGAGAACGAAGGTAA (30) |
| rs2826399 | TCCATTCCACTCAACACACG (3)<br>CAATGACACCCAAAAATTCG (4) | CGCAGACATATACAGGCCATA (31)<br>CGTCTGTCGTGCATGTTGA (32) |
| rs2828312 | TTGAAAGATATCCACTCTCTTCTTCA (5)<br>GGAGAGTATGCTTTACATATCAGGAA (6) | CCACTCTCTTCTTCATTCTGGA (33)<br>CAGGAAACTTCTCTTATGGTTCTTC (34) |
| rs2830585 | TGATGGTTGCTGACACTTGG (7)<br>TGCAGTTTGCCTATCGTCAC (8) | GGGAGCAGCGTACCATTG (35)<br>CCCTGCTCCCAGAAACAAC (36) |
| rs1153292 | TGACTTCCAGAGGGATGAGC (9)<br>TCCAAACACAGCCTAGTCACC (10) | GGATGAGCTGGCCTCTTTTT (37)<br>ATGTGGAACAATGCCACTGA (38) |
| rs1805127 | GCCCTTTCTGACCAAGCTGT (11)<br>AGAAGCCGAAGAATCCCAGT (12) | TGTGGCAGGAGACAGTTCAG (39)<br>CGTAGAGGGCCTCCAGCTT (40) |
| rs2226357 | ATGAAATGTTTGGTATGTTGACCA (13)<br>GTCGTACCCAATGTCCGAGT (14) | CCACATGATTAGCATTTTGTAGC (41)<br>TGTCCGAGTTTATTGGTCCTT (42) |
| rs2836015 | CAGGAGAAATTTCCATTTTTCAA (15)<br>AGAATAAAGCCTTCTTCAAATGAG (16) | AAAATATGCCTTGTATTTCATATTCAT (43)<br>AGAATAAAGCCTTCTTCAAATGAG (44) |
| rs2836016 | GGCCATTGTTGCAGTTTCTT (17)<br>CCTAGGAAAAAGAAGGAAGAGAGA (18) | TTCTTTGTGCTTTTCCTGGAG (45)<br>GCTGTAAATGGCAATTAGATCA (46) |
| rs2836019 | ACCTGCTTGCTGTGGAATTT (19)<br>AGGCTCCTCTCTGCCTGTCT (20) | TTGGGTTATGTCAACATGCAG (47)<br>TCTCTGCCTGTCTTATTCAGCTC (48) |
| rs2836021 | CCTGGTGTGCTCATTTCAGA (21)<br>TTTTTCACCTTAAAATACCACCAA (22) | GCTGCTTGCTGTTTTCTGC (49)<br>CAGTCTATCAAAGCATGTTCAGG (50) |
| rs2837501 | GGCCTTTTATATTCGACATGGA (23)<br>GCACAGGTTACACGTTGTGTC (24) | TCTCACCCACAGAGGCTTTT (51)<br>GATTTCACAGTTCCCTCTGCTT (52) |
| rs2839596 | TTTTCACTCTAAACTGTTCTGTCCA (25)<br>TAGTGGGAGTGGCTTCTTGG (26) | CACATTTTGGCAGCTGGTG (53)<br>GCATGGAGAGCACCTGAATC (54) |
| rs2839320 | TCCACCTGCCTGTTAGGAAC (27)<br>ATGTGATGTGTCCAGCTCGT (28) | GGAACCAATTTTAATGATAAACTCAA (55)<br>CGTCCAGCTCCAGGATGAT (56) |

Amplification of SNP Alleles

SNP alleles at each locus were amplified from the DOP-PCR products and the genomic DNA samples using locus-specific primers. Occasionally, some samples showed increased background that can be eliminated by an additional round of nest PCR using primers that are nested within the corresponding starting PCR products. Locus-specific starting and nest PCR primers for each locus are listed in Table 1. The starting and nest PCR reactions were carried out using a "step-down" protocol, including one cycle of 94° C. 3 min, 10 cycles of 94° C. 30 sec, 65° C. 30 sec with a decrease of 1.5° C. per cycle and 72° C. 30 sec, and 30 cycles of 94° C. 30 sec, 51° C. 30 sec and 72° C. 30 sec, followed by a final extension at 72° C. for 10 min; the PCR Primer Extension Analysis Approximately 50 ng of a locus-specific PCR product was mixed with 0.1 µM extension primer, 50 µM locus-specific ddNTP and dNTP mix (see Table 2), 1× extension reaction buffer and 2U Thermo Sequenase DNA polymerase (Amersham) in 20 µl for the primer extension reaction. The reaction cycles included an initial denaturation at 95° C. for 3 min followed by 50 cycles of 96° C. 10 sec and 58° C. 1 min. Primer extension products were analyzed using the WAVE Nucleic Acid Fragment Analysis System (Transgenomic) under a fully denaturing condition according to the manufacturer's instruction.

TABLE 2

Chromosome 21q SNP locus-specific single base extension (SBE) primers

| refSNP ID | Alleles | SBE primer (5'→3') (SEQ ID NO) | Nucleotide mix | Product length (bp) |
|---|---|---|---|---|
| rs2824397 | G/T | GAGCTGTCTTTTGTACTCTGCT (57) | ddGTP, dATP, dTTP | 23 (G)/29 (T) |
| rs2826399 | C/T | CAGCGTTAATATTGTCCATTTCA (58) | ddTTP, dCTP, dGTP | 24 (T)/28 (C) |
| rs2828312 | A/T | GGATCTAAATGGGTGGGTAAAG (59) | ddATP, dCTP, dTTP | 23 (A)/28 (T) |
| rs2830585 | C/T | GGGCATGAGACTGCAGGAG (60) | ddTTP, dCTP, dGTP | 20 (T)/23 (C) |
| rs1153292 | A/C | TTCTTGGACAGCTTTTCCAG (61) | ddCTP, dATP, dGTP | 21 (C)/24 (A) |
| rs1805127 | C/T | CCTCCAGCTTGCCGTCAC (62) | ddTTP, dCTP, dGTP | 19 (T)/22 (C) |
| rs2226357 | C/G | TGTCCGAGTTTATTGGTCCTTA (63) | ddGTP, dATP, dCTP | 23 (G)/27 (C) |
| rs2836015 | A/G | GAGAAATGCAGTTTTCTATGATGAA (64) | ddATP, dCTP, dGTP, dTTP | 26 (A)/30 (G) |
| rs2836016 | A/G | TTTGTGCTTTTCCTGGAGGT (65) | ddGTP, dATP | 21 (G)/23 (A) |
| rs2836019 | C/T | GCCAGTAGAGAGGCTAAGTGTCA (66) | ddTTP, dCTP, dGTP | 24 (T)/26 (C) |
| rs2836021 | A/G | AAGCATGTTCAGGTATCCTCTTC (67) | ddGTP, dATP, dTTP | 24 (G)/26 (A) |
| rs2837501 | C/T | CACAGAGGCTTTTTGGCA (68) | ddCTP, dTTP, dGTP | 19 (C)/23 (T) |
| rs2839596 | A/G | TTTGTTCACTACAAGTCCCTTAAAA (69) | ddATP, dCTP, dGTP, dTTP | 26 (A)/31 (G) |
| rs2839320 | C/T | GATAAACTCAAGGATGGCATCT (70) | ddTTP, dATP, dCTP, dGTP | 23 (T)/27 (C) |

Sequencing

The locus-specific PCR products were labeled with ABI PRISM BigDye (Applied Biosystems) using the locus-specific nest PCR primers (see Table 1) according to the manufacturer's instruction and sequenced on ABI PRISM 3700 sequencer (Applied Biosystems)

Example 2

Characterization of Visible Regions of Normal Chromosome 21

This example illustrates a method according to the invention for haplotype determination of a human chromosome, specifically, human chromosome 21 [Hattori, et al., Nature 405: 311-321 (2000)]. The strategy involves several technical steps, including microdissection of chromosome regions, universal amplification of dissected DNA, reverse FISH for identification of the genomic origins of the chromosome regions, region-specific genomic DNA/gene array and genome-wide SNP array analysis. Single copies of dissected chromosome 21 may be obtained from a transformed normal lymphoblast cell line. A suitable cell line is GM 03657 (Coriell Institute; normal karyotype of 46,XY).

Metaphase cells are spread on clean 25×50 mm coverslips and G-banded for microdissection, as described in our previous studies [Kao, et al., Proc. Natl. Acad. Sci. U.S.A. 88: 1844-1848 (1991)]. The chromosome and the chromosome region to be dissected are identified under the microscope and subseqently dissected with a sharp glass needle using an Eppendorf TransferMan NK2 manipulator attached to the microscope. The dissected chromosome may be delivered in a collection buffer for the universal amplification. In this example, single copies of the whole long arm of chromosome 21 (21q) and a series of regions of 21q with different sizes are isolated for the sake of illustration.

Since the amplification template is only a single copy of a chromosome region, several rounds of amplification are needed to generate sufficient amount of DNA for the following analysis. DOP PCR has been successfully used to amplify a single dissected chromosome region for FISH [Meltzer, et al., Nat. Genet. 1: 24-28 (1992)], and to amplify genomic DNA for genotyping analysis [Cheung, et al., Proc. Natl. Acad. Sci. U.S.A. 93: 14676-14679 (1996); Cheung, et al., Proc. Natl. Acad. Sci U.S.A. 93: 14676-14679(1996)].

Briefly, a single copy of chromosome 21 is treated with topoisomerase I (Promega) for releasing the tension of the double-helix DNA chains, and then with 5-8 cycles of initial amplification using T7 polymerase (USB) and a degenerate primer (5'-CCGACTCGAGNNNNNNATGTGG-3' (SEQ ID NO:75), followed by 25 cycles of the first round PCR with Taq DNA polymerase and the same primer. The PCR products are then treated with shrimp alkaline phosphatase (USB) to clean up the primers and unmatched DNA templates, and then used as the templates for the second round PCR amplification with fresh prepared buffer, enzyme and the primer; if needed the third round PCR in similar fashion.

Alternatively, dissected DNA is digested with a restriction enzyme and the resulting DNA fragments are ligated with a linker adaptor on their both ends, which serves as the specific primer binding site, then a specific PCR can be performed. Since primer-specific PCR is used, dissected chromosome regions can be repeatedly amplified to produce large amount of DNA with high quality and low background, which can be directly used for FISH and for array analysis.

The amplified DNA can also be cloned for construction of sequencing-ready genomic libraries, from which each clone can be directly sequenced. If a chromosome region of interest is separately digested with two different restriction enzymes for adding linker adaptors for amplification, the sequence coverage for this chromosome region may increase significantly. This is perhaps thus far the most efficient way to clone abnormal regions and to produce large stable and pure genomic clones from the abnormal regions for genomic analysis. As an alternative to PCR-based amplifications, MDA may be utilized to amplify dissected single chromosomes. This method uses phage phi29 DNA polymerase to amplify DNA at 30° C., which can amplify a large amount of high-molecular weight genomic DNA.

Reverse FISH may then be performed to confirm the genomic origins of the amplified DNA. The amplified DNA is labeled with fluorescence-labeled nucleotides by PCR, randomly priming or nick-translation (for MDA products) as probes, and hybridized to normal metaphase chromosome spreads following standard protocols. FISH results may be analyzed using an image analysis program (Cytovision, Applied Imaging); with the genomic origins of the dissected chromosomes identified by locating the hybridization signals on the specific chromosome regions.

Once the genomic origin of a dissected chromosome fragment is identified, analysis using high-resolution, region-specific genomic/gene arrays is performed to characterize the dissected fragment. For example, a series of chromosome 21 region-specific arrays may be obtained from NimbleGen Systems, a representative provider of such arrays. A proprietary hybridization system, including protocols, buffers, hybridization cassettes, hardware, and temperature control instrumentation that generate highly reproducible and sensitive hybridizations are commercially available. These protocols have been optimized to require minimum amounts of sample, while providing a hybridization volume that can be continually mixed over the time-course of the incubation. Such arrays are useful to reveal the gene content, genomic tag content and the potential breakpoint positions, if any, of the dissected chromosome.

SNP and haplotype analysis is then carried out using arrays currently available for detecting SNPs, such arrays being divided into two groups: locus-specific SNP arrays and the genome-wide global SNP arrays. A particularly well-suited array is the Affymatrix human SNP array (Genechip Mapping 100K set) that is a global SNP array containing over 100,000 SNPs genome-wide. Since only a single chromosome is analyzed for each test, the array of SNP alleles detected in that chromosome represents the actual haplotype of the chromosome. Haplotype blocks and the corresponding haplotype tag SNPs in each analyzed chromosome region can be determined by matching detected SNP alleles with the haplotype block and SNP maps in HapMap and other databases.

Example 3

Characterization of Lymphoma-Specific Chromosome Abnormalities

Lymphomas are a group of heterogeneous hematological malignancies which often show chromosome aberrations. Certain lymphoma-specific chromosome abnormalities have been identified, such as t(8;14)(q24;q32) and t(11;14)(q13;q32) translocations in Burkitt lymphoma and Mantle cell lymphoma, respectively. However, the genomic features of many other clonal chromosome aberrations that are frequently seen in lymphomas, particularly marker chromosomes, remain unknown. Such aberrations can be readily characterized by the invention. In this example, the inventors characterized two cytogenetically undistinguishable chromosome deletions in only two cells from two unrelated pediatric patients, respectively, to demonstrate the proof of principle. This example involves several technical steps, including microdissection of chromosome regions, universal amplification of dissected DNA, reverse FISH for identification of the genomic origins of the chromosome regions, and region-specific genomic DNA/gene array analysis.

Figure 4:
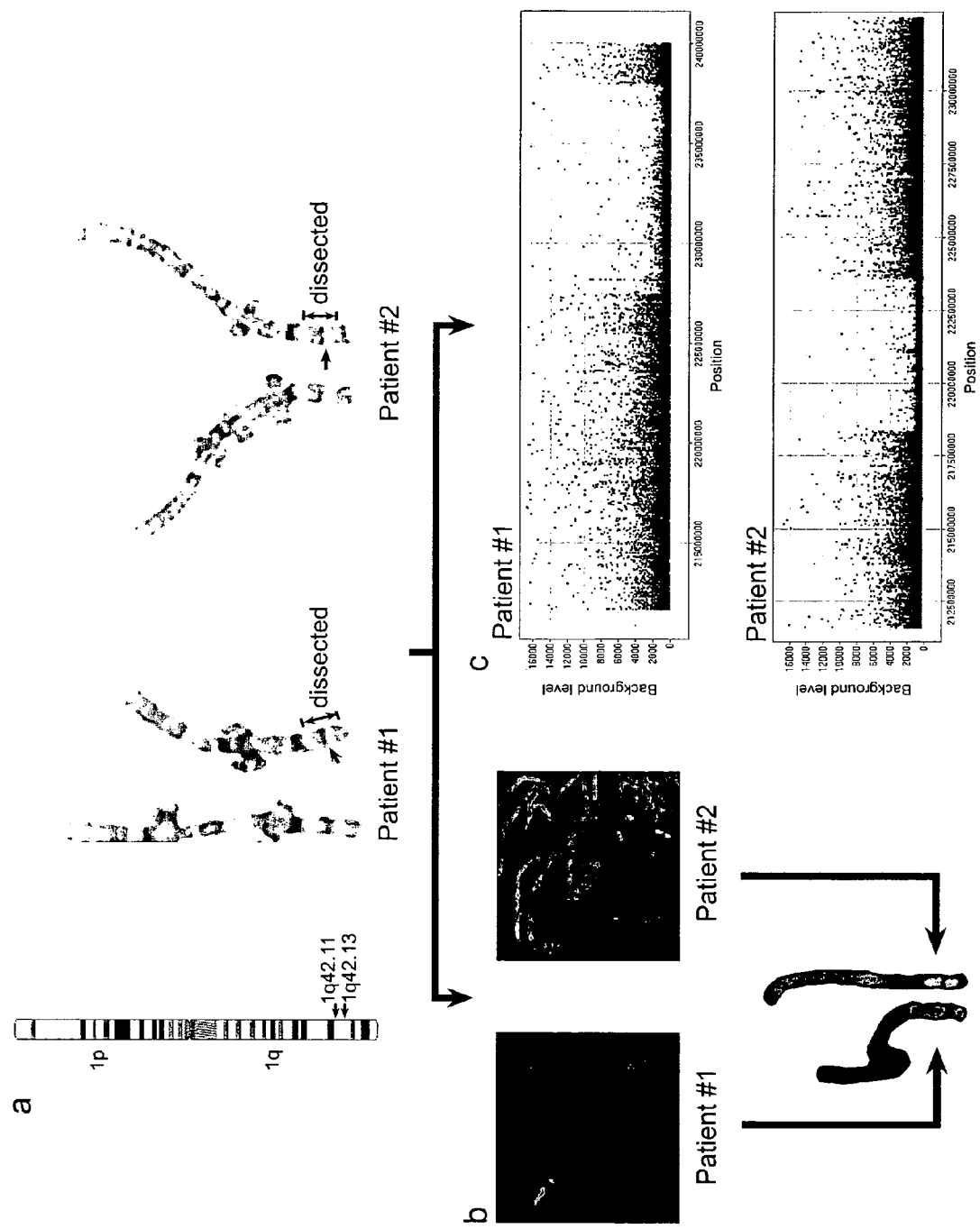
FIG. 4. FISH and micro-array analysis of aberrant human chromosome 1 in two unrelated pediatric patients.

Each visible chromosome region containing a deletion was individually dissected from a single cell from each patient and was amplified in analogous fashion to that described in the previous Example section. The amplified abnormal regions were used as probes in reverse FISH to identify the corresponding genomic origins which were determined to be1q42.11-1q42.13 (FIGS. 4a & b). The deleted regions are not translocated to the other part of the genome. In addition, the FISH results indicate that the deletions are apparently not identical, showing different sizes and positions ((FIG. 4b, the deletions showed as "gaps" in the FISH picture). Amplified DNA from the dissected region was then subjected to high-resolution, chromosome 1q42 region-specific oligonucleotide genomic DNA array analysis. This analysis clearly revealed two non-overlapped deletions in different patients, consistent with the FISH findings: the patient #1 has a more distal 10.6 Mb deletion between 227.4-238 Mb, which contains 67 known genes, and the patient #2 has a more proximal 5.3 Mb deletion between 218.3-223.6 Mb, which contains 52 known genes (FIG. 4c, the deletions are indicated by the background level of 1000). The resolution of this array analysis can be as high as 1 kb, and the findings using only a single cell from each patient unambiguously define two cytogenetically undistinguishable different deletions and provide detailed information for further clinical assessment of the two patients. This is the first example of applying single-copy microdissected chromosomes to the high-resolution DNA array analysis.

Those skilled in the art will recognize, or be able to ascertain using no more then routine experimentation, numerous equivalents to the specific polypeptides, nucleic acids, methods, assays and reagents described herein. Such equivalents are considered to be within the scope of this invention and encompassed by the following claims.

What is claimed is:

1. A method of identifying a genomic feature present within a visible chromosome region, comprising steps of:
   (a) micro-dissecting a single copy of a chromosome to obtain a visible chromosome region containing a genomic feature;
   (b) amplifying said visible chromosome region to obtain amplified single chromosome DNA; and
   (c) subjecting said amplified single chromosome DNA to micro-array analysis using a micro-array to identify the genomic feature present within said visible chromosome region.

2. The method according to claim 1 wherein the genomic feature is genomic DNA size, gene content, DNA breakpoint, or DNA polymorphism.

3. The method according to claim 1 wherein the genomic feature is a single nucleotide polymorphism (SNP).

4. The method according to claim 1 wherein the genomic feature comprises a plurality of single nucleotide polymorphisms (SNPs) corresponding to a SNP haplotype of the visible chromosome region.

5. The method according to claim 1 wherein said micro-array is a genomic array, gene array, or single nucleotide polymorphism (SNP) array.

6. The method according to claim 1 wherein said micro-array is an oligo- or genomic clone-based comparative genomic hybridization (CGH) array.

7. The method according to claim 1 wherein the visible chromosome region comprises a visible aberration.

8. The method according to claim 1 wherein said chromosome micro-dissected in step (a) is obtained from a single cell isolated from a population of heterogeneous cells.

9. The method according to claim 1 wherein said chromosome micro-dissected in step (a) is a human chromosome.

10. The method according to claim 1 wherein said chromosome micro-dissected in step (a) is an abnormal chromosome obtained from a single dividing cancer cell.

11. The method according to claim 1 wherein said chromosome micro-dissected in step (a) is a normal chromosome obtained from a single dividing cell.

12. The method according to claim 1 wherein the amplification recited in step (b) is carried out by polymerase chain reaction (PCR), multiple displacement amplification (MDA), or a combination thereof.

13. The method according to claim 1 including the further step of performing reverse fluorescence in situ hybridization (FISH) on a chromosome preparation using said amplified single chromosome DNA to identify a genomic origin of said visible chromosome region, said genomic origin at least in part directing selection of an array in the micro-array analysis of step (c).

14. A method of identifying at least one single nucleotide polymorphism (SNP) present within a visible chromosome region, comprising steps of:
    (a) micro-dissecting a single copy of a chromosome to obtain a visible chromosome region containing a SNP;
    (b) amplifying said visible chromosome region to obtain amplified single chromosome DNA; and
    (c) subjecting said amplified single chromosome DNA to SNP micro-array analysis using a SNP micro-array to identify the SNP present within said visible chromosome region.

15. The method according to claim 14 wherein a plurality of single nucleotide polymorphisms (SNPs) are identified by the method, said plurality of SNPs corresponding to a SNP haplotype of the visible chromosome region.

16. The method according to claim 14 wherein steps (a)-(d) are repeated using a haploid chromosome homologue such that SNP haplotypes of a homologue chromosome set are identified by the method.

17. A method of determining the identity of a single nucleotide polymorphism (SNP) at a SNP locus present within a visible chromosome region, comprising steps of:
    (a) micro-dissecting a single copy of a chromosome to obtain a visible chromosome region containing a SNP locus;
    (b) amplifying said visible chromosome region to obtain amplified single chromosome DNA; and
    (c) subjecting said amplified single chromosome DNA to SNP analysis to determine the identity of a single nucleotide polymorphism (SNP) at the SNP locus present within the visible chromosome region.

18. The method according to claim 17 wherein the SNP analysis of step (c) is performed by subjecting said amplified single chromosome DNA to micro-array analysis.

19. The method according to claim 17 wherein step (c) is repeated to obtain a plurality of single nucleotide polymorphisms (SNPs), said plurality of SNPs corresponding to a SNP haplotype of the visible chromosome region.

20. The method according to claim 17 wherein steps (a)-(c) are repeated using a corresponding haploid chromosome homologue such that SNP haplotypes of a chromosome homologue set are identified by the method.

* * * * *